United States Patent [19]

Mackay

[11] Patent Number: 4,874,492
[45] Date of Patent: Oct. 17, 1989

[54] ANALYSIS OF SAMPLES BY ELECTROPHORESIS USING A CHARGE COUPLED DEVICE

[75] Inventor: Craig D. Mackay, Cambridge, Great Britain

[73] Assignee: Astromed Limited, Cambridge, Great Britain

[21] Appl. No.: 203,482

[22] Filed: Jun. 6, 1988

Related U.S. Application Data

[63] Continuation-in-part of Ser. No. 867,494, May 28, 1986, abandoned.

[30] Foreign Application Priority Data

May 29, 1985 [GB] United Kingdom ................. 8513538

[51] Int. Cl.⁴ ............................................. G01N 27/26
[52] U.S. Cl. .............................. 204/182.8; 204/299 R
[58] Field of Search .............. 204/299 R, 182.8, 180.1

[56] References Cited

U.S. PATENT DOCUMENTS 4,666,578  5/1987  Yamamoto ................. 204/299 R X

FOREIGN PATENT DOCUMENTS 125691  11/1984  European Pat. Off. .
143205   6/1985  European Pat. Off. .
WO87/07033 11/1987 PCT Int'l Appl. .

OTHER PUBLICATIONS

Toda et al, "Microcomputer-Aided Two-Dimensional Densitometry", Electrophoresis '83, (1984), pp. 139–146.

Smith et al, "Fluorescence Detection in Automated DNA Sequence Analysis", Nature, vol. 321 (Jun. 12, 1986), pp. 674–679.

Bonazzola et al, "Charged Coupled Devices as Autoradiography Imagers", IEEE Transactions on Nuclear Science, vol. NS-32, No. 1 (Feb. 1985), pp. 567–570.

Sutherland et al, "Electronic Imaging System for Direct and Rapid Quantitation of Fluorescence from Electrophoretic Gels", Analytical Biochemistry 163 (1987), pp. 446–457.

Primary Examiner—John F. Niebling
Assistant Examiner—John S. Starsiak, Jr.
Attorney, Agent, or Firm—Lee & Smith

[57] ABSTRACT

Light from the pattern of spots of bands resulting from electrophoresis is detected by a two-dimensional charge coupled device, visualization of the spots or band being achieved by irradiating the gel with a U/V source to stimulate fluorescent markers preferably applied before running of the gel. The charge coupled device is cooled to suppress thermal dark current and, more particularly, to improve sensitivity and dynamic range.

12 Claims, 2 Drawing Sheets

ANALYSIS OF SAMPLES BY ELECTROPHORESIS USING A CHARGE COUPLED DEVICE

RELATED APPLICATION

This invention is a continuation-in-part of my application Ser. No 867,494 filed May 28, 1986, now abandoned with the title "Improvements in or relating to electrophoresis".

FIELD OF THE INVENTION

The invention relates to a method of analysing samples by use of electrophoresis and to apparatus for carrying out said method.

BACKGROUND OF THE INVENTION

Electrophoresis is a separation technique in which molecules or other units are separated, eg for analysis or purification purposes, by application of an electric field. This causes differential migration of the units, the rate of migration of each unit depending on its charge and frictional resistance (which is related to its size and shape). The technique is used to separate mixtures e.g. of proteins or DNA fragments, with the mixture being located on a suitable porous gel, typically of starch, agarose or polyacrylamide, referred to herein as an electrophoretic gel. Differential migration on application of the electric field results in either a one dimensional array of bands or a two dimensional array of spots. The resulting bands or spots can be detected by a number of techniques, including the following:

1. By staining with a suitable dye, rendering the bands or spots opaque and visible.
2. By staining with fluorescent markers or labels which emit light when stimulated by an U/V radiation source.
3. By use of radioactive markers or labels, e.g. using the technique known as autoradiography.

Analysis of electrophoresis results by these techniques has serious limitations. With stained dyes viewed in transmission, the faintest spots or bands have to be detected against a bright background, while the darkest spots or bands may transmit so little light that they are impossible accurately to measure with conventional detectors such as T.V. cameras or photographic films. Likewise, fluorescent marker dyes produce high level of fluorescent background since the dyes also bind to the gel as well as to the spots or bands. This makes it hard to see weak spots or bands as they are easily lost in the fluorescent background.

Autoradiography has all the problems associated with the handling of radioactive materials, plus poor resolution and extremely long visualisation times, of the order of days to weeks. However, autoradiography is able to detect the presence of smaller quantities of the components, e.g. protein or DNA fragments, than hitherto known techniques using dyes or markers. In particular, the use of fluorescent markers has been considered impractical for detection of components present in very small amounts, due to problems of sensitivity. However, protein and DNA fragments are frequently present only in these small amounts.

It is a primary object of this invention to provide a highly sensitive method for effecting analysis of the results of electrophoresis, without incurring the disadvantages associated with autoradiography techniques.

SUMMARY OF THE INVENTION

According to one aspect of the present invention, there is provided a method of analysing samples by use of electrophoresis comprising the steps of:

treating the samples with fluorescent marking material so that components of the sample are fluorescently marked;

applying the samples to an electrophretic gel;

running the gel to effect electrophoresis causing differential migration of different components;

irradiating the gel with a U/V source to render the marked components visible;

detecting the pattern of light emanating from the marked components by means of a light sensitive charge coupled device (CCD), said CCD being a silicon CCD having a two-dimensional detector array; and cooling the CCD to a temperature less than $-25$ degrees C. during detection.

According to another aspect of the present invention, there is provided apparatus for analysing fluorescently marked samples by electrophoresis comprising:

a source of U/V radiation for illuminating an electrophoretic gel to which the fluorescently marked samples have been applied;

means to control running of gel to effect electrophoresis, causing differential migration of different components of the samples giving rise to a pattern of light due to illumination of the gel by the U/V source; and means for detecting the pattern of light; wherein the detecting means comprises:

a light sensitive silicon charge coupled device (CCD) having a two-dimensional detector array; and means for cooling the CCD during detection to a temperature less than $-25$ degrees C.

By way of explanation, and as is generally understood and known in the electronics art, the term CCD applies to a device which permits packets of electronic charge to be transferred across an integrated circuit structure essentially without loss. Some CCDs are light sensitive and the charge packet is generated as a result of light falling on the integrated circuit, and it is with light sensitive CCDs that the present invention is concerned.

Light sensitive CCDs may be used to generate an electronic representation of a two-dimensional image. If the CCD is a linear array of pixels then each line of the image is measured sequentially and the linear CCD is moved across the image to sample each line in turn. This procedure is acceptable if the image is opaque and detected by its absorption of a bright light (for example illuminated by a controllable light source) where each of the sequential exposures can be short. However when the light levels to be detected are low the total time to record the image is unacceptably long, and two-dimensional CCDs, having a two-dimensional array of pixels, are used. In this case, a single exposure will record all the image elements in the full image. The sensitivity advantage over a linear CCD array is clearly apparent. The consequence of this is that applications that use linear CCD arrays are essentially high light level applications.

At room temperatures the dark current (signal generated in the absence of any light input by the device because it is warm) limits operation of CCDs to about $10^{-1}$ lux to $-10^{-2}$ lux. CCDs may be cooled, and it is known that cooling down to −40 degrees C. can reduce dark current, although it has been considered that reduction of temperature beyond this point ceases to be advantageous ("Charge-coupled Devices and Systems", edited by Howes and Morgan, pages 272/3, Wiley Interscience, 1979). The present invention is based on use of cooling to below −25 degrees C., preferably to below −40 degrees C. and down as far as −160 degrees C., which improves light sensitivity and increases dynamic range. It is this, at least in part, which makes practicable the low light level highly sensitive method of analysis of the invention. Thus, in contrast to the method of autoradiography proposed in U.S. Pat. No 4,665,312 and the method proposed by Toda et al, in the article concerning Microcomputer-aided two-dimensional densitometry in Electrophor '83 Adv. Methods Biochem. Clin. Appl., Proc. Int. Conf. 4th, Meeting (1983), pages 139 to 146, and by Toda et al in the article concerning a method of microcomputer-aided two-dimensional densitometry appearing in Electrophoresis (Weinheim, Fed. Repub. Ger.) 5(1), 42–7 (1984), the invention for the first time makes possible a highly accurate method of analysing the results of separation by electrophoresis in which fluorescent markings can be utilised.

Hitherto the use of fluorescent labels in electrophoresis has not been able to give results of good sensitivity and so has not been practicable for use in detecting small quantities of materials such as protein and DNA fragments. The normal conventional way of using fluorescence is to treat fluorescence as a variation on staining procedures such as Coamassie or silver staining: a gel is run, unpacked and soaked in a fluorescent material and then unattached fluorescent dye is washed out. This method gives good fluorescence but very high background because fluorescent material gets stuck in the gel irrespective of whether material that is supposed to be fluorescently labelled is present.

Hitherto problems have also been associated with fluorescent labelling of material before carrying out electrophoresis, principally because this produces very weak fluorescence. There are very few references to this method in the literature: it is treated as a method that will not work because of sensitivity problems. The present invention enables this approach to be used and works extremely well, giving sensitivity levels comparable with those achieved by autoradiography without any of the problems or the time needed for radiography or staining.

In accordance with the invention, while under certain conditions adequate results can be achieved with cooling to −25 degrees C., but sensitivities can be significantly increased with further cooling down as far as −160 degrees C. Typical operation temperatures are in the range −40°C to −120 degrees C.

A suitable CCD system for use in this invention is the CCD 2000 Imaging System produced by Astromed Limited, Cambridge, United Kingdom. This system operates in slow-scan readout and can be operated as a frame transfer CCD and so can be used to detect light from moving components during separation by electrophoresis. This is achieved by transferring charge distribution across the CCD in synchronism with movement of the components, as will be described in more detail below.

Alternatively, separation by electrophoresis may be halted; the pattern of light from the separating components detected, and electrophoretic separation resumed.

The charge coupled device may be coated with one or more materials which absorb radiation of one wavelength and emit electromagnetic radiation of another wavelength, whereby electromagnetic radiation of wavelengths to which the charge coupled device is not sensitive can be detected indirectly.

The invention enables analysis of the results of electrophoresis to be speeded up significantly as compared with autoradiography techniques, as well as increasing the accuracy obtainable and permitting use of smaller sample volumes than has been possible hitherto. The invention also greatly increases the range of integrated spot or band intensities contained within one array that can be handled, and alows much more accurate quantitation of the amount of say protein or DNA in each separated spot or band.

BRIEF DESCRIPTION OF DRAWINGS

The invention is further explained with reference to the accompanying drawings, in which.

DESCRIPTION OF PREFERRED EMBODIMENT

Figure 1:
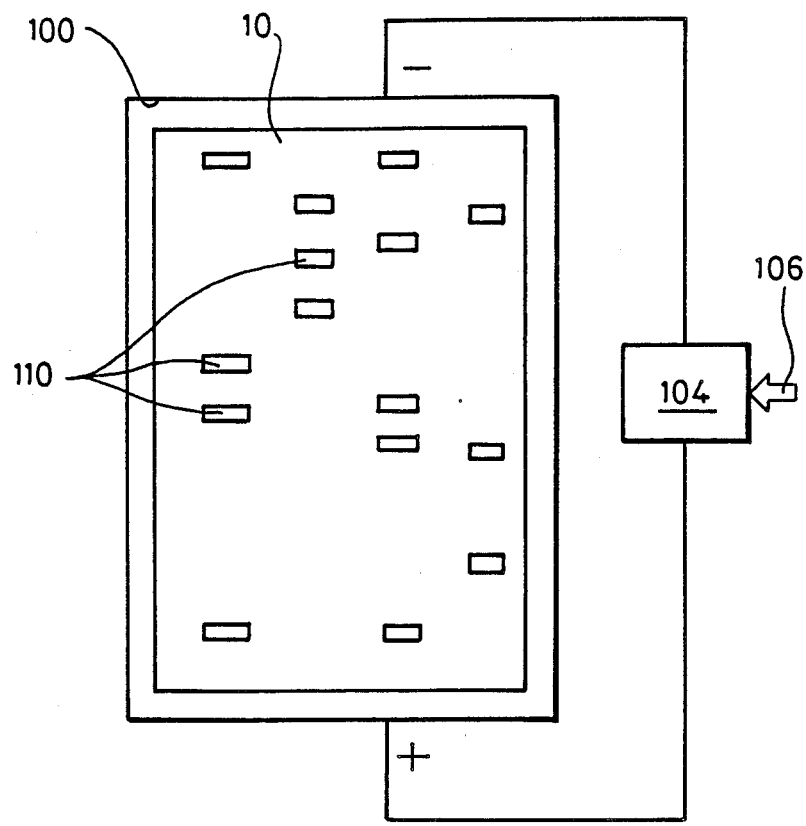
FIG. 1 schematically illustrates electrophoresis separation apparatus.

The electrophoresis apparatus of FIG. 1 comprises a tray-like container 100 containing an electrophoretic gel 10, typically of starch, polyacrylamide or agarose. A voltage source 104 is employed to establish a controlled electric field across the gel, in the direction of the length of the tray, as indicated by the positive and negative signs. In the present case, the voltage source may itself be connected, via cable 106, to a computer forming part of the analysis apparatus of FIG. 2, so that the electrophoresis process is controllable in accordance with the requirements of the method of analysis.

The gel is typically used for separating samples of DNA fragments into a series of bands, or for separating protein mixtures which have already been partially separated by iso-electric focussing into an array of spots. In either case, the materials are generally treated with fluorescent marking material prior to application to the gel, e.g. using conventional techniques such as disclosed in "Gel Electrophoresis of Proteins: a Practical Approach" Edited by B D Hames and D Rickwood, IRL Press, 1981, e.g. on p 49.

The top of the gel is thus either loaded with a first stage iso-electrically focussed gel rod (for two-dimensional analysis) in which e.g. mixtures of proteins treated with fluorescent marking material such as MDPF (2-methoxy-2,4 diphenyl-3(2H) furanone) are contained, or the gel includes a number, e.g. several sets of four wells into which are located samples e.g. of DNA fragments tagged with a fluorescent dye such as FITC (fluorescein isothiocyanate) to be analysed by electrophoresis. When the electric field is applied across the tray, differential migration of different components of the samples occurs, in the direction of the length of the tray. The starting, stopping and speed of the separating process is controllable by the voltage source 104. After the gel has been run for at least a minimum length of time, the different components are separated into discrete spots or bands 110.

Normally, of course, the spots or bands 110 would not be visible, but when the samples are pre-labelled with a fluorescent marker the spots or bands become visible when the gel is irradiated by the source of U/V radiation. This source forms part of the analysis apparatus of FIG. 2.

Figure 2:
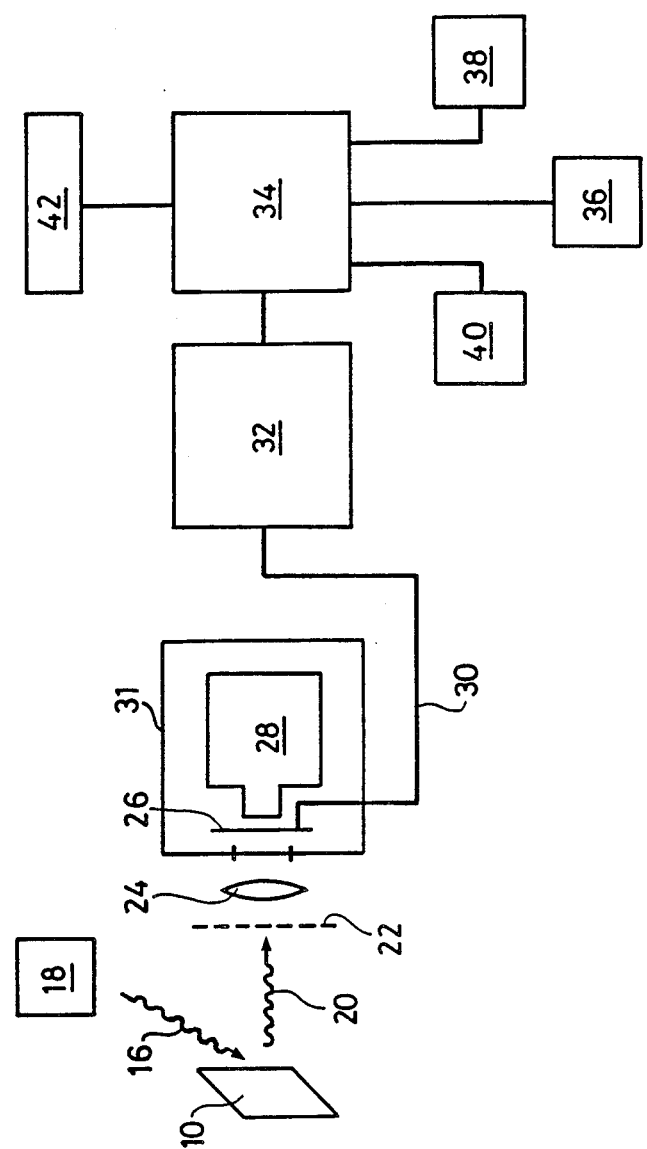
FIG. 2 is a schematic illustration of apparatus in accordance with the invention for analysing the results of the electrophoresis.

Thus, referring to FIG. 2, the illustrated analysis apparatus comprises the gel 10 bearing a two dimensional array of spots or bands produced by electrophoretic separation of sample mixtures applied thereto. The fluorescently labelled spots or bands emit light when stimulated by shorter wavelength light 16 from ultra violet source 18.

The resulting emitted light 20 is detected by a cooled charge coupled device detector system, comprising a CCD 2000 Imaging System produced by Astromed Limited, Cambridge, United Kingdom. In the drawing, the basic Astromed imaging system comprises the items 26, 28, 30 and 32. The light 20 first passes through a filter 22 to select the emitted light against the shorter wavelength flood light. The transmitted or emitted light is then imaged by a lens 24 onto a cooled solid-state-charge coupled device detector 26 (P8600 series CCD made by EEV Ltd) contained in an environmental enclosure 31 and mounted to the outside of a cold box 28 cooled with liquid nitrogen. Cooling could be effected, instead, by means of a Sterling cycle or other mechanical or electrical cooler. Cooling of the detector 26 is effected down to an operating temperature of less than $-25$ degrees C., preferably between $-40$ and $-120$ degrees C., and possibly down as low as about $-160$ degrees C.

The CCD 26, mounted inside the sealed enclosure 30 and cooled by the cold box 28 to the operating temperature, is connected by fine wires to a connector and hence a cable 30 to a driver electronics module included in the CCD 2000 imaging system. This electronics unit, in accordance with the operating characteristics of the system, generates bias and clock signals necessary to drive the CCD in its slow-scan mode of operation. The electronics also processes the output signal from the CCD such in a way as to minimise the overall system read-out noise and to maximise the system dynamic range. The electronics unit includes an analog to digital converter such as the Zeltex ZAD 7400 unit which gives true 16 bit digital output (65536 grey levels).

The driver electronics unit is connected by a data cable to an interface board also included in the CCD 2000 System, which is located inside a host computer 34 and connected directly to the computer input/output bus. The computer 34 may be e.g. an IBM PC/AT with EGA screen and keyboard 36 and operates with a resident operating system such as the AT & T UNIX system marketed by Microport Inc, and an application software suite such as the Astromed Command Language.

The computer 34 may have a variety of peripherals attached to it, as the application demands. These may include a disc drive 38 for floppy or hard disks such as drives manufactured by IBM and supplied with IBM computers, magnetic tape decks such as those made by Cifer Inc. and an image display unit 40 such as that made and marketed by Astromed Ltd.

The software in the computer 34 allows data to be taken, displayed, archived and analysed to give a distribution of detected bands of the gel to be determined, together with the detailed properties of the bands such as position, shape, size, orientation and intensity. The data so obtained is output on to a printer 42 such as the Canon LBP-A2 laser printer or an Epson FX 80 dot matrix printer or archived to disk or magnetic tape for storage or to allow comparison with band distributions obtained for other gels.

The above described system has a number of advantages and properties as follows:

1. The cooled CCD system has the widest dynamic range of any two dimensional imaging system, in excess of 50,000:1. In transmission mode, the high dynamic range of the system allows the detection of spots and bands that are much fainter than is possible with low dynamic range detectors such as T.V. cameras (with dynamic ranges from 64:1 to 256:1 typically), while still allowing extremely bright spots and bands to be measured accurately.

2. The exceptionally low read-out noise (typically 6 electrons rms) together with the high quantum efficiency (greater than about 40% peak) allows the detection in fluorescence mode of spots or bands that are much fainter than are otherwise detectable. This is because it is possible to integrate the signal from the gel for many minutes or hours without adding dark signal or read-out noise at the low operation temperatures (down to about 125° K.).

3. The resolution on the gel obtainable may be enhanced as follows. When a scene is imaged onto a frame transfer CCD detector, a two dimensional charge distribution is established that exactly follows the light distribution falling upon it. Normally the accumulated charge distribution is read out at the end of the exposure by moving the two dimensional charge distribution across the device and reading it out one line at a time. However if, throughout the exposure, the 2-D charge distribution is transferred across the device and the light falling on the CCD is moved across the device, in synchronism with the charge already accumulated, then it is possible to obtain an image of arbitrary length in the direction of movement. As signal moves along a column, each pixel in the column will contribute in turn to the signal, so that the detection sensitivity of different pixels of the column is averaged in the signal in each pixel of output. Thus the pixels of output from one column of the CCD give a column of output that is completely uniform from the detector point of view and therefore reduces the need for flat fielding the data.

Movement of the charge distribution across the CCD in synchronism with movement of the light source being monitored (the electrophoretic movement) is controlled by the control computer and driver electronics. Thus, this method simply requires the computer to output software generated control signals to control the electrophoresis power supply level that determines the rate of movement of the spots or bands.

4. Calibration chemicals (typically proteins or DNA segments) are often added to 1-D and 2-D electrophoresis gels to act as calibration standards of mass and charge. In fluorescence work it can be difficult to match the signal levels from the calibration spots or bands so that they do not swamp the faint signals to be detected. The wide spectral coverage of the CCD detector (400 mm–1100 mm) allows the calibration chemicals to be tagged with fluorescent dyes that fluoresce at a wavelength different enough from that of the dye used for the principal sample chemicals, for their colours to be distinguished by placing filters in front of the detector.

Such a procedure allows precision calibration to be achieved of the charge and mass axes of the gel because of the exceptional geometric stability of the CCD detector.

5. The excellent geometric fidelity of the CCD system (discussed in 4. above) allows the creation of data sets that are absolutely calibrated rather than relatively calibrated as is normally the case. The procedures permit the establishment of reference databanks of the processed output of the gel/detector/computer analysis system that may be easily searched for features different to or in common with other gels or sets of gels already processed and analysed. These procedures allow gels to be run to detect differences in the gel spot or band map due to variations in the composition of the sample caused by, for example, disease or infection or the additions of pharmaceuticals (in blood serum or organ protein electrophoresis), by injury or accident (the detection of organ-specific proteins in blood serum protein electrophoresis), by contamination (in food samples, as part of food processing procedures) etc.

6. In DNA sequencing by the dideoxy (enzymatic) method, four types of DNA segments are produced (called A,C,G and T). If these are tagged with a fluorescent dye such as FITC (fluorescein isothiocyanate) and the four components run in four separate parallel 1-D tracks in an electrophoresis gel then the cooled CCD detector is able to detect segments in low concentrations because of the great sensitivity of the detector in fluorescent mode.

The simultaneous detection of the four tracks side by side allows the sequencing to be performed particularly accurately.

Other methods of detecting the DNA segments may be used such as blotting the sequencing gel and using fluorescently marked DNA probes to illuminate a selected subset of the segments. These can then be detected with the cooled CCD Imaging System as before.

A serious problem in running DNA sequencing gels is that the resolution of the gel increases with the distance a band has moved from the sample starting point, so bands in the middle of the gel may be resolved only half as well as those at the bottom of the gel (assuming it is being used from top to bottom). Uniquely with the CCD it is possible to obtain the advantages of extreme sensitivity of a two dimensional detector while clocking the CCD in synchronism with the moving bands while the gel is actually being run, as in the drift scan mode described in 3. above. Placing the detector near the bottom or higher resolution end of the gel to track (electrically, by clocking) the bands as they pass towards the edge of the gel allows all the bands to be detected with the same high resolution. This permits more accurate sequencing because of the higher resolution. It requires the running of a single gel (normally separate gels are used to allow the poorly-resolved top section of the gel to be properly resolved) saving time, effort and expense. The geometric and photometric precision of the cooled CCD system permits the immediate extraction of the sequence results with the minimum delay and the minimum subsequent imaging processing. It is particularly important, in this respect, to note that analysis can take place during the running of the gel.

7. In some applications the almost complete lack of sensitivity to wavelengths less than 4000 Angstroms is a great advantage (such as when using a UV light source to generate fluorescence in the visible wavelength range). In others extended blue and UV response would be helpful when the light to be detected as part of the procedures described herein is of wavelength less than 4000 Angstroms. Enhanced blue and UV sensitivity may be obtained by coating the CCD with a thin (few microns thick) layer of a mixture of laser dyes in a solid matrix. The dye layer absorbs short wavelength radiation and re-emits it in the visible region of the spectrum where part of this re-emission is detected by the CCD. Each laser dye absorbs a photon and re-emits it with a wavelength only a few hundred Angstroms greater, so a cocktail of laser dyes is required to shift an incident photon by greater wavelength differences. Efficiencies approaching 50% of the visible or red detective quantum efficiency of the device are achieved in practice. Care has to be taken to select laser dyes that are not affected by high ambient lighting conditions if they are to be easy to use. The use of laser dyes as outlined above gives a detector that has high quantum efficiency over a very wide wavelength range.

I claim:

1. A method of analysing biological samples by use of electrophoresis comprising the steps of:
   treating the samples with fluorescent marking material so that components of the samples are fluorescently marked;
   applying the fluorescently marked samples to an electrophoretic gel;
   running the gel to effect electrophoresis causing differential migration of different components;
   irradiating the gel with an U/V source to render the marked components visible;
   detecting the pattern of light emanating from the marked components by means of a light sensitive charge coupled device (CCD), said CCD being a silicon CCD having a two-dimensional detector array and being operated in slow scan mode; and
   cooling the CCD to a temperature less than −25 degrees C. During detection.

2. A method according to claim 1, in which the CCD is cooled to a temperature in the range −40 degrees C. to −160 degrees C.

3. A method according to claim 2, in which the CCD is cooled to a temperature of about −120 degrees C.

4. A method according to claim 1, in which the samples are marked with a fluorescent material which emits electromagnetic radiation at a first wavelength and a calibration chemical is mixed with the material, the calibration chemical being marked with a fluorescent material which emits electromagnetic radiation at a second wavelength, and the wavelengths detected by the CCD are varied to enable the calibration chemical to be distinguished from the material subject to electrophoresis.

5. A method according to claim 1, in which the running of the gel to effect separation by electrophoresis is halted, the pattern of light from separated components is detected, and running of the gel is then resumed.

6. A method according to claim 1, in which the charge coupled device is a frame transfer CCD and the pattern of light is detected during electrophoretic movement, charge packets being shifted through the CCD in the same direction as and in synchronism with movement of the pattern of light falling on the CCD due to the electrophoretic movement.

7. A method according to claim 6, in which the CCD is used to detect bands or spots contained in the pattern of light when they are brought to a predetermined location by the electrophoresis.

8. A method according to claim 1, in which the output from the CCD is compared with the results of previous electrophoretic separations stored in a databank.

9. A method according to claim 1, wherein the samples contain small quantities of protein or DNA.

10. Apparatus for analysing fluorescently marked biological samples by electrophoresis, comprising:
- a source of U/V radiation for illuminating an electrophoretic gel to which the fluorescently marked samples have been applied;
- means to control running of gel to effect electrophoresis, causing differential migration of different components of the samples giving rise to a pattern of light due to illumination of the gel by the U/V source; and
- means for detecting the pattern of light; wherein the detecting means comprises:
  - a light sensitive silicon charge coupled device (CCD) having a two-dimensional detector array and being operated in slow scan mode; and
  - means for cooling the CCD during detection to a temperature less than $-25$ degrees C.

11. Apparatus according to claim 10, in which the charge coupled device is a frame transfer CCD.

12. Apparatus according to claim 11, having driving circuits for the charge coupled device adapted to drive the charge coupled device in synchronism with movement of the light falling thereon due to electrophoretic movement.

* * * * *